United States Patent
Marciano et al.

(10) Patent No.: US 12,073,923 B2
(45) Date of Patent: Aug. 27, 2024

(54) METHODS AND SYSTEMS FOR DETERMINATION OF THE NUMBER OF CONTRIBUTORS TO A DNA MIXTURE

(71) Applicants: Michael Marciano, Manlius, NY (US); Jonathan D. Adelman, Mexico, NY (US)

(72) Inventors: Michael Marciano, Manlius, NY (US); Jonathan D. Adelman, Mexico, NY (US)

(73) Assignee: Syracuse University, Syracuse, NY (US)

( * ) Notice: Subject to any disclaimer, the term of this patent is extended or adjusted under 35 U.S.C. 154(b) by 1791 days.

(21) Appl. No.: 15/780,673

(22) PCT Filed: Dec. 2, 2016

(86) PCT No.: PCT/US2016/064711
§ 371 (c)(1),
(2) Date: Jun. 1, 2018

(87) PCT Pub. No.: WO2017/096219
PCT Pub. Date: Jun. 8, 2017

(65) Prior Publication Data
US 2018/0355347 A1    Dec. 13, 2018

Related U.S. Application Data

(60) Provisional application No. 62/349,219, filed on Jun. 13, 2016, provisional application No. 62/262,560, filed on Dec. 3, 2015.

(51) Int. Cl.
*G01N 33/48* (2006.01)
*C12Q 1/6851* (2018.01)
(Continued)

(52) U.S. Cl.
CPC ........... *G16B 40/20* (2019.02); *C12Q 1/6851* (2013.01); *G16B 30/00* (2019.02); *G16B 40/00* (2019.02); *B01L 7/52* (2013.01); *G06F 3/00* (2013.01)

(58) Field of Classification Search
CPC ........ G16B 40/20; G16B 30/00; G16B 40/00; C12Q 1/6851
See application file for complete search history.

(56) References Cited

U.S. PATENT DOCUMENTS 10,957,421 B2 * 3/2021 Marciano ............... G16B 40/00
2009/0148835 A1  6/2009 Cave et al.
(Continued)

OTHER PUBLICATIONS

Vervier et al. Large-scale machine learning for Metagenomics sequence classification. Bioinformatics, Nov. 20, 2015, vol. 32, No. 7, pp. 1023-1032.*

(Continued)

*Primary Examiner* — Russell S Negin
(74) *Attorney, Agent, or Firm* — David L. Nocilly; Bond Schoeneck & King PLLC

(57) ABSTRACT

A system configured to characterize a number of contributors to a DNA mixture within a sample, the system comprising: a sample preparation module configured to generate initial data about the DNA mixture within the sample; a processor comprising a number of contributors determination module comprising a machine-learning algorithm configured to: (i) receive the generated initial data; (ii) analyze the generated initial data to determine the number of contributors to the DNA mixture within the sample; and an output device configured to receive the determined number of contributors from the processor, and further configured output information about the received determined number of contributors.

12 Claims, 6 Drawing Sheets

(51) Int. Cl.
  *G01N 33/50* (2006.01)
  *G16B 30/00* (2019.01)
  *G16B 40/00* (2019.01)
  *G16B 40/20* (2019.01)
  *B01L 7/00* (2006.01)
  *G06F 3/00* (2006.01)

(56) References Cited

U.S. PATENT DOCUMENTS

2014/0052383 A1    2/2014   Larson et al.
2016/0162636 A1    6/2016   Marciano et al.

OTHER PUBLICATIONS

Hoorfar et al. Diagnostic PCR: validation and sample preparation are two sides of the same coin. APMIS, vol. 112, pp. 808-814. (Year: 2004).*

Lee, et al. "Inferring enthnicity from mitochondrial DNA sequence," BMC Proceedings, Apr. 28, 2011 (Apr. 28, 2011), vol. 5, Suppl. 2, pp. 1-9, entire document.

International Search Report Form PCT/ISA/210, International Application No. PCT/US2016/064711, pp. 1-6, Dated Dec. 3, 2015.

* cited by examiner

METHODS AND SYSTEMS FOR DETERMINATION OF THE NUMBER OF CONTRIBUTORS TO A DNA MIXTURE

CROSS-REFERENCE TO RELATED APPLICATION

This application claims priority to U.S. Provisional Patent Application Ser. No. 62/262,560, filed on Dec. 3, 2015 and entitled "Machine Learning Approach to Identify the Number of Contributors in a DNA Sample," and U.S. Provisional Patent Application Ser. No. 62/349,219, filed on Jun. 13, 2016 and entitled "PACE: Probabilistic Assessment for Contributor Estimation—A Probabilistic Machine Learning-Based Assessment of the Number of Contributors in DNA Mixtures," the entire disclosures of which are incorporated herein by reference.

FIELD OF THE INVENTION

The present disclosure is directed generally to methods and systems for identifying nucleic acid in a sample and, more particularly, to methods and systems for characterizing the number of contributors to a DNA mixture.

BACKGROUND

At the core of the genetic identification field, particularly in regard to forensic applications and clinical/medical research, is the challenge of DNA mixture interpretation. A DNA sample mixture can be defined as a mixture of two or more biological samples, and mastery of their interpretation can greatly impact the course of criminal investigations and/or quality of intelligence. The ability to separate or "deconvolute" the individual donors from a DNA mixture remains one of the most critical challenges in the field of forensic DNA analysis.

Several metrics are required to accurately interpret and deconvolute DNA mixtures; a selection of the most critical include the number of contributors, the minimum expected heterozygote balance, the ratio of contributors, the amount of DNA template and the probabilities of allele drop-out and drop-in. Specifically, the number of contributors is widely considered the most critical component in leading to an accurate DNA mixture deconvolution, in large part due to the deconvolution's sensitivity to whichever number of contributors is assumed. Likelihood-based deconvolution methods require the (potentially erroneous) assumption that the number of contributors is known by the analyst. Indeed, the assumption of the number of contributors can greatly affect the resulting conclusions; establishing the number of contributors permits the analyst to set a range of potential alleles at a particular locus within the sample and proceed with mixture deconvolution, but the use of incorrect assumptions regarding the number of contributors can have (at times extremely) adverse effects on the resulting likelihood ratios and subsequently, the mixture interpretation as a whole. Therefore, making high-probability estimates of the number of contributors in a given mixture should be considered a vital component of DNA mixture deconvolution.

However, existing methods to estimate the number of contributors to a DNA mixture are inadequate and/or inefficient. Existing methodologies, for example, overestimate or underestimate the number of contributors, or require hours of processing to achieve an outcome.

Accordingly, there is a need in the art for methods and systems that perform complicated DNA mixture interpretation, particularly with regard to more accurately determining the number of contributors to a DNA mixture.

SUMMARY OF THE INVENTION

The present disclosure is directed to methods and systems for determining the number of contributors to a DNA mixture. The method and systems described herein probabilistically infer the number of contributors in a mixed DNA sample using a machine learning approach. The conclusions generated are based on the use of both categorical (qualitative) data such as allele labels, dye channels and continuous and discrete (quantitative) data such as stutter rates, peak heights, heterozygote balance, and mixture ratios that describe the DNA sample. The method is computationally inexpensive, and results are obtained within seconds using a standard desktop or laptop computer with a standard processor.

According to an aspect is a system configured to characterize a number of contributors to a DNA mixture within a sample. The system includes: a sample preparation module configured to generate initial data about the DNA mixture within the sample; a processor comprising a number of contributors determination module, wherein the number of contributors determination module comprises a machine-learning algorithm configured to: (i) receive the generated initial data; (ii) analyze the generated initial data to determine the number of contributors to the DNA mixture within the sample; and an output device configured to receive the determined number of contributors from the processor, and further configured output information about the received determined number of contributors.

According to an embodiment, the machine-learning algorithm comprises a support vector machine algorithm.

According to an embodiment, the output device comprises a monitor.

According to an embodiment, the sample preparation module comprises amplification of DNA within the sample. According to an embodiment, the sample preparation module comprises amplification of one or more DNA markers within the sample.

According to an aspect is a system configured to characterize a number of contributors to a DNA mixture within a sample, the system comprising a processor configured to receive data about the DNA within the sample, and further configured to analyze, using a machine-learning algorithm, the received data to determine the number of contributors to the DNA mixture within the sample According to an embodiment, the system further includes a sample preparation module configured to generate the data about the DNA within the sample. According to an embodiment, the sample preparation module comprises amplification of DNA within the sample. According to an embodiment, the sample preparation module comprises amplification of one or more DNA markers within the sample.

According to an embodiment, the system further includes an output device in communication with the processor, the output device configured output information about the received determined number of contributors. According to an embodiment, the output device comprises a monitor.

According to an embodiment, the machine-learning algorithm comprises a support vector machine algorithm.

These and other aspects of the invention will be apparent from the embodiments described below.

BRIEF DESCRIPTION OF THE DRAWINGS

The present invention will be more fully understood and appreciated by reading the following Detailed Description in conjunction with the accompanying drawings, in which.

DETAILED DESCRIPTION OF EMBODIMENTS

There is a continued need for methods and systems that perform DNA mixture interpretation in both a time-effective and cost-effective manner. Accordingly, the present disclosure is directed to methods and systems for determining the number of contributors within a DNA mixture using a machine learning approach. The conclusions generated are based on the use of both categorical (qualitative) data such as allele labels, dye channels and continuous and discrete (quantitative) data such as stutter rates, peak heights, heterozygote balance, and mixture ratios that describe the DNA sample. The method is computationally inexpensive, and results are obtained within seconds using a standard desktop or laptop computer with a standard processor According to an embodiment, the method employs a machine learning algorithm for one or more steps. Machine learning refers to the development of systems that can learn from data. For example, a machine learning algorithm can, after exposure to an initial set of data, be used to generalize; that is, it can evaluate new, previously unseen examples and relate them to the initial training data. Machine learning is a widely-used approach with an incredibly diverse range of applications, with examples such as object recognition, natural language processing, and DNA sequence classification. It is suited for classification problems involving implicit patterns, and is most effective when used in conjunction with large amounts of data. Machine learning might be suitable for DNA mixture analysis, as there are large repositories of human DNA mixture data in electronic forma. Patterns in this data are often non-obvious and beyond the effective reach of manual analysis, but can be statistically evaluated using one or more machine learning algorithms as described or otherwise envisioned herein.

Figure 1:
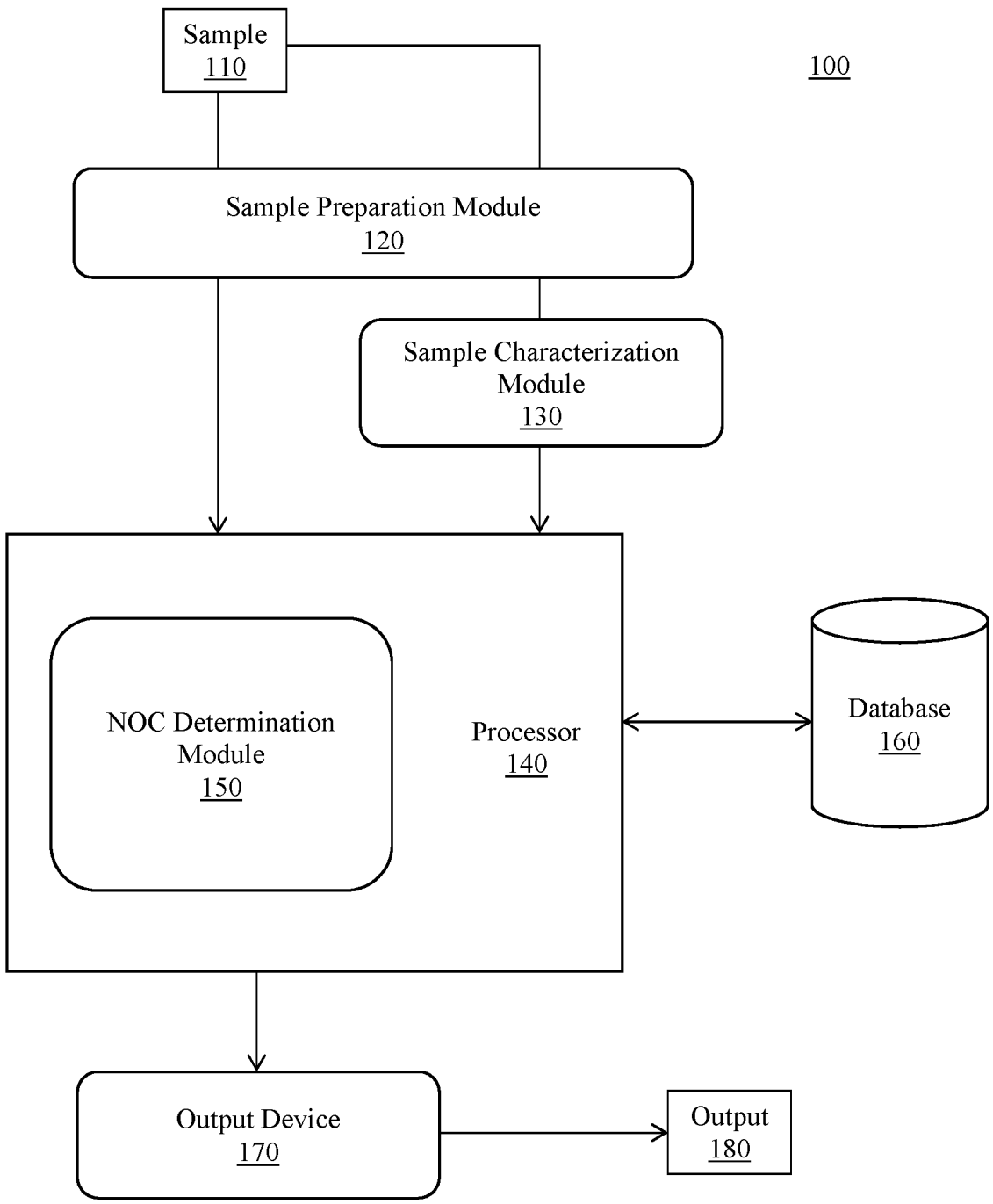
FIG. 1 is a schematic representation of a system for DNA mixture analysis, in accordance with an embodiment, in accordance with an embodiment.

Referring to FIG. 1, in one embodiment, is a system 100 for characterizing the number of DNA sources contributing to a sample 110, where sample potentially 110 contains DNA from one or more sources. Sample 110 can previously be known to include a mixture of DNA from two or more sources, or can be an uncharacterized sample. Sample 110 can be obtained directly in the field and then analyzed, or can be obtained at a distant location and/or time prior to analysis. Any sample that could possibly contain DNA therefore could be utilized in the analysis.

According to an embodiment, system 100 can comprise a sample preparation module 120. Sample preparation module 120 can be, for example, a device, step, component, or system that prepares the obtained sample for analysis. For example, sample preparation module 120 may comprise DNA isolation, extraction, separation, and/or purification. According to an embodiment, sample preparation module 120 may include any modification of the sample to prepare that sample for analysis.

According to an embodiment, system 100 can optionally comprise a sample characterization module 130. For example, DNA present in the sample can be characterized by, for example, capillary electrophoresis based fragment analysis, sequencing using PCR analysis with species-specific and/or species-agnostic primers, SNP analysis, one or more loci from human Y-DNA, X-DNA, and/or at DNA, or any other of a wide variety of DNA characterization methods. According to advanced methods, other characteristics of the DNA may be analyzed, such as methylation patterns or other epigenetic modifications, among other characteristics. According to an embodiment, the DNA characterization results in one or more data files containing DNA sequence and/or loci information that can be utilized for identification of one or more sources of the DNA in the sample, either by species or individually within a species (such as a particular human being, etc.).

According to an embodiment, system 100 comprises a processor 140. Processor 140 can comprise, for example, a general purpose processor, an application specific processor, or any other processor suitable for carrying out the processing steps as described or otherwise envisioned herein. According to an embodiment, processor 140 may be a combination of two or more processors. Processor 140 may be local or remote from one or more of the other components of system 140. For example, processor 140 might be located within a lab, within a facility comprise multiple labs, or at a central location that services multiple facilities. According to another embodiment, processor 140 is offered via a software as a service. One of ordinary skill will appreciate that non-transitory storage medium may be implemented as multiple different storage mediums, which may all be local, may be remote (e.g., in the cloud), or some combination of the two.

According to an embodiment, processor 140 comprises or is in communication with a non-transitory storage medium 160. Database 160 may be any storage medium suitable for storing program code for executed by processor 140 to carry out any one of the steps described or otherwise envisioned herein. Non-transitory storage medium may be comprised of primary memory, secondary memory, and/or a combination thereof. As described in greater detail herein, database 160 may also comprise stored data to facilitate the analysis, characterization, and/or identification of the DNA in the sample 110.

According to an embodiment, processor 140 comprises a number of contributors (NOC) determination algorithm or module 150. NOC determination algorithm or module 150 may be configured to comprise, perform, or otherwise execute any of the functionality described or otherwise envisioned herein. According to an embodiment, NOC determination algorithm or module 150 receives data about the DNA within the sample 110, among other possible data, and utilizes that data to predict or determine the number of contributors to the DNA within that sample, among other outcomes. According to an embodiment as described in greater detail herein, NOC determination algorithm or module 150 comprises a trained or trainable machine-learning algorithm configured or configurable to determine the number of contributors to the DNA within sample 110.

According to an embodiment, system 100 comprises an output device 170, which may be any device configured to or capable of generating and/or delivering output 180 to a user or another device. For example, output device 170 may be a monitor, printer, or any other output device. The output device 170 may be in wired and/or wireless communication with processor 140 and any other component of system 100. According to yet another embodiment, the output device 170 is a remote device connected to the system via a network. For example, output device 170 may be a smartphone, tablet, or any other portable or remote computing device. Processor 140 is optionally further configured to generate output deliverable to output device 170, and/or to drive output device 170 to generate and/or provide output 180.

As described herein, output 180 may comprise information about the number of contributors to the DNA found in the sample, and/or any other received and/or derived information about the sample.

Figure 2:
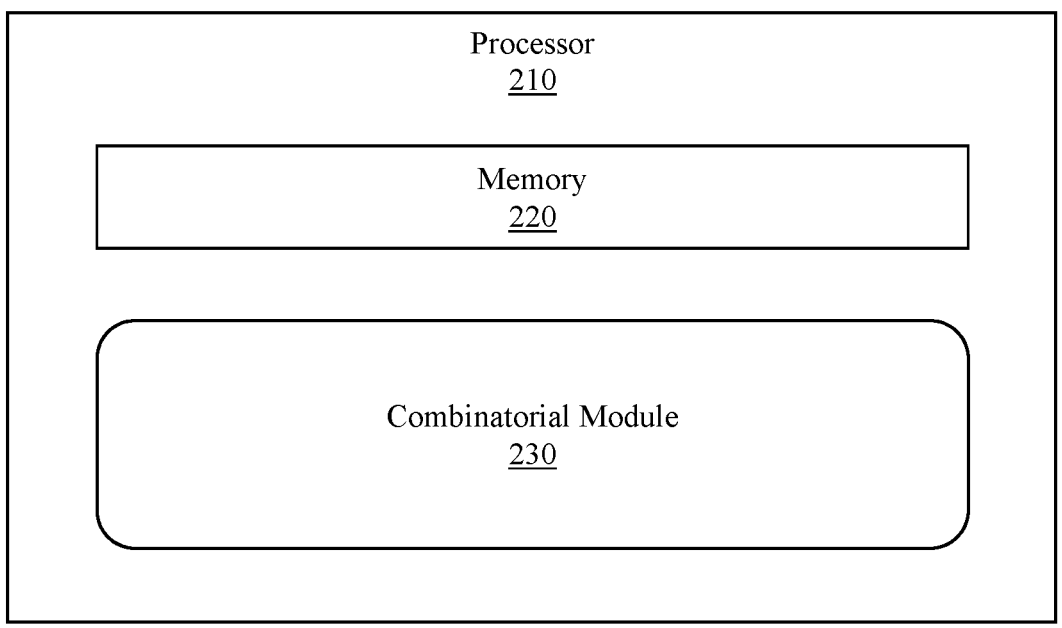
FIG. 2 is a schematic representation of a system for DNA mixture analysis, in accordance with an embodiment.

Referring to FIG. 2, in one embodiment, is a schematic representation of a system 200 for characterizing the number of contributors to a DNA mixture of a sample. The sample can previously be known to include a mixture of DNA from two or more sources, or can be an uncharacterized sample. The sample can be obtained directly in the field and then analyzed, or can be obtained at a distant location and/or time prior to analysis. Any sample that could possibly contain DNA therefore could be utilized in the analysis.

According to an embodiment, system 200 comprises a processor 210. Processor 210 can comprise, for example, a general purpose processor, an application specific processor, or any other processor suitable for carrying out the processing steps as described or otherwise envisioned herein. According to an embodiment, processor 210 may be a combination of two or more processors. Processor 210 may be local or remote from one or more of the other components of system 210. For example, processor 210 might be located within a lab, within a facility comprise multiple labs, or at a central location that services multiple facilities. According to another embodiment, processor 210 is offered via a software as a service. One of ordinary skill will appreciate that non-transitory storage medium may be implemented as multiple different storage mediums, which may all be local, may be remote (e.g., in the cloud), or some combination of the two.

According to an embodiment, processor 210 comprises a non-transitory storage medium 220. Storage medium 220 may be any storage medium suitable for storing program code for executed by processor 210 to carry out any one of the steps described or otherwise envisioned herein. Non-transitory storage medium may be comprised of primary memory, secondary memory, and/or a combination thereof. As described in greater detail herein, Storage medium 220 may also comprise stored data to facilitate the analysis, characterization, and/or identification of the DNA in the sample.

According to an embodiment, processor 210 comprises a number of contributors (NOC) module 230. NOC determination module 230 may be configured to comprise, perform, or otherwise execute any of the functionality described or otherwise envisioned herein. According to an embodiment, NOC determination algorithm or module 230 receives data about the DNA within a sample, among other possible data, and utilizes that data to predict or determine the number of contributors to the DNA within that sample, among other outcomes. According to an embodiment as described in greater detail herein, NOC determination algorithm or module 230 comprises a trained or trainable machine-learning algorithm configured or configurable to determine the number of contributors to the DNA within a sample.

EXAMPLE

The classification performances of six machine learning algorithms as described or otherwise envisioned herein were compared, and the top-performing algorithm's model was evaluated against the current state of the art in the field of number of contributors (NOC) classification. The algorithm resulted in greater than 98% accuracy in identifying the number of contributors in a DNA mixture of up to four contributors. Comparative results showed three-person mixtures had a classification accuracy improvement of over 6% compared to existing methods, and that four-person mixtures had a classification accuracy improvement of over 20%. The methodology accomplished classification of mixtures of up to four contributors in less than one second using a standard laptop or desktop computer. Considering the high classification accuracy rates, as well as the significant time commitment required by the current state of the art versus seconds required by a machine learning-derived model, the approach described herein provides a promising means of estimating the number of contributors and, subsequently, leads to improved DNA mixture interpretation.

As described above, the methodology is computationally inexpensive and results can be obtained in 10 seconds or less using, for example, a standard desktop or laptop computer with 6-8 GB RAM and an Intel i5 1.9 gHz processor, although many other computational parameters are possible, including both significantly smaller and greater RAM, and/or significantly slower and faster processing speeds. According to an embodiment, the method achieves this through the use of machine learning and, in contrast to approaches that use Markov Chain Monte Carlo methods, leverages an initial training and testing data set to build the model. According to an embodiment, this imparts both speed and reproducibility onto the end user, with all of the computational heavy lifting done during data acquisition and model creation.

Materials and Methods

Data Acquisition and Exportation

The system was trained, tested and validated using electronic data (.fsa files) obtained from 1405 non-simulated DNA mixture samples comprised of 1-4 contributors and generated from a combination of 16 individuals. The set was obtained through publically available data sets and validation data provided by collaborators. This set of 1405 samples included 35 different DNA template amounts from 0.0125 ng to 10 ng (0.0125, 0.025, 0.05, 0.0625, 0.075, 0.1, 0.125, 0.15, 0.2, 0.25, 0.3, 0.4, 0.5, 0.6, 0.7, 0.8, 1.0, 1.2, 1.3, 1.5, 1.6, 1.7, 2.0, 2.5, 3.0, 3.3, 3.5, 4.0, 5.0, 6.0, 7.0, 7.5, 8.0, 9.0, 10.0 ng) and 28 different ratios of contributors (1.6:3:1:1, 1.6:3:1:2, 1.6:3:2:1, 1.6:3:2:2, 1.6:6:1:1, 3:3:1:1, 3:6:1:1, 1.6:12:1, 1.5:3:1, 1.5:3:2, 1.5:6:1, 1.6:3:4, 12:1:1, 1:3:1/3: 1:1/1:3, 3:1:2, 3:1:4, 3:2:1, 3:3:1, 3:4:1, 6:1:1, 6:3:1, 1:0, 1:1, 1:19/19:1, 1:2/2:1, 1:4/4:1, 1:9/9:1, 10:1). These samples were previously amplified using the AmpFLSTR® Identifiler® PCR Amplification Kit (ThermoFisher Scientific Inc.) (28 cycles) with subsequent detection performed on five different 3130/3100 Genetic Analyzers (ThermoFisher Scientific Inc.). Fragment analysis was performed using GeneMarkerHID® v2.8.2 (SoftGenetics® LLC) using a threshold of 10 rfu without stutter filters. All data were conservatively pre-processed by an analyst to remove artefacts such as dye blobs and electrical spikes. Data were exported from GeneMarkerHID® v2.8.2 (SoftGenetics® LLC) for further analysis using PACE software. PACE-based preprocessing of the exported fragment data included the application of stutter filters (see TABLE 1) and an analytical threshold. The analytical threshold was applied based on the level of baseline noise encountered at each sample-locus combination; stochastic thresholds were not employed.

TABLE 1

FNSSI-applied Identifiler stutter filters DKL.

| Locus | Stutter filter |
|---|---|
| D8S1179 | 0.08 |
| D21S11 | 0.09 |
| D7S820 | 0.08 |
| CSF1PO | 0.09 |
| D3S1358 | 0.11 |
| TH01 | 0.05 |
| D13S317 | 0.08 |
| D16S539 | 0.1 |
| D2S1338 | 0.11 |
| D19S433 | 0.16 |
| vWA | 0.13 |
| TPOX | 0.05 |
| D18S51 | 0.17 |
| AMEL | 0 |
| D5S818 | 0.07 |
| FGA | 0.15 |

Data Partitioning

Generalization refers to a model's ability to predict outcome values for previously unseen data. A fully-trained machine learning algorithm, on its own, cannot be generalized to new, unfamiliar data. Such an algorithm is capable of creating a model that makes good predictions only if future data are selected from the initial training library; it may well have learned specific patterns only found in the training data by chance, and erroneously leverages those patterns to aid with classification. This is synonymous to a curve-fitting problem in which a high-degree polynomial is used to fit generally linear data; such a choice may well result in a high correlation coefficient, but as soon as even one additional data point is added the coefficient's value can plummet. Such a scenario highlights the problem of overfitting a model to data. To ensure generalization, the learner must instead be both trained and tested, and it is the resulting testing accuracy—not the training accuracy—that serves to validate the learned model. Such an approach requires that the initial data set—in this case, the library of DNA mixtures—must correspondingly be partitioned into completely separate training and testing subsets. For all modeling efforts herein, the training data set was created by randomly selecting 75% of the initial data, with the other 25% used for testing how generalizable the learned model is.

Machine learning algorithms contain hyperparameters; these can be loosely thought of as knobs that tune an algorithm and thereby affect its behavior. Some hyperparameters can have a non-trivial impact on the resulting training time or even classification accuracy. Any attempt to tune these hyperparameters and thereby maximize an algorithm's classification accuracy must therefore always be accompanied by a further partitioning of training data, to ensure that data used for "tuned" algorithm validation aren't also used to validate the final model. All hyperparameter tuning in the current example fulfills this requirement via utilization of 5-fold cross-validation on the training data set.

Feature Scaling

Learning algorithms make use of data instances, each one of which has a corresponding feature vector. In this context, features can be considered data categories such as peak height, allele count per locus, etc. Most machine learning algorithms cannot appropriately utilize the raw features in this vector because feature scales can be wildly different from one another. The template DNA feature, for example, has mean and variance several orders of magnitude smaller than those of the maximum peak height feature. Distinct means and variances can lead to some features' importance being artificially inflated by learning algorithms, which are spending disproportionate amounts of time minimizing the larger errors produced by the features with the larger variances. While many researchers choose to resolve this concern by simply normalizing feature data via min-max scaling to a range of [0, 1], some learning algorithms learn model weights more quickly and are more robust in the face of data outliers if features are instead standardized using the following equation:

$$X_{std}^{(i)} = \frac{X^{(i)} + \mu_x}{\sigma_x} \quad \text{Eq. (1)}$$

where $X^{(i)}$ is a given feature, $\mu_x$ is the feature's mean, and $\sigma_x$ is the corresponding standard deviation. All feature scaling in the current example was performed using Equation 1.

Feature Selection

The 'curse of dimensionality' refers to a characteristic of classification problems in which the continual addition of new features to a feature vector ultimately leads to decreased accuracy of the resulting classification model. Just as data are partitioned into a training set and a testing set to allow model validation and avoid data overfitting, so too must the feature vector be set to an optimal size—not too small, where vital information with predictive value is ignored, but not too large, where additional dimensions in the problem's feature space lead to a very high training accuracy and a very low testing accuracy: a hallmark of overfitting. It becomes of great importance, then, to only include features that strongly contribute to the subsequent classification problem, and to remove features that fail to contribute.

One metric that can estimate a feature's classification importance is Kullback-Leibler divergence (see Equation 2), which is a measure of the reduction in entropy of the class variable (in this case, the true number of contributors) after the value for the feature is observed:

$$D_{KL}(P\|Q) = \sum_i P(i) \log \frac{P(i)}{Q(i)}. \quad \text{Eq. (2)}$$

All candidate features are ranked by divergence, and any candidate feature with a divergence below 0.01 is removed prior to machine learning. Calculations of Kullback-Leibler divergence were performed using the Weka Knowledge Analysis Environment, version 3.8, although other methods are possible.

Machine Learning Algorithms

No single machine learning algorithm is ideally suited for all classification problems. The best-suited algorithm often depends on the size, quality, and characteristics of the associated training data. This example evaluates five candidate machine learning algorithms, although, notably, other machine learning algorithms may be utilized for this process.

1. The k-Nearest Neighbors (k-NN) algorithm determines an instance's class based on the most common class of its neighbors. Specifically, each object is classified by a majority vote of its nearest k neighbors, with the object then assigned to the most common class among those neighbors.

2. The Classification and Regression Trees (CART) algorithm, a variant on the $C_{4.5}$ algorithm, is one of the most commonly used decision tree classifiers. The decision tree itself is a foundational machine learning concept, in which feature space is continually subdivided into smaller regions of roughly uniform values, and in which the leaves of the tree represent the possible classes into which an object can be classified. Decision trees often provide high-accuracy models, but can also overfit data more frequently and are therefore potentially worse than the other candidate algorithms at generalizing to unseen data.

3. The Multinomial Logistic Regression (Logit) algorithm should not be confused with the statistical regression model in which the dependent variable is categorical. This classifier is instead an extension of that model, capable of generalizing to multiclass problems.

4. The Multilayer Perceptron (MLP) algorithm is an artificial neural network in which backward propagation of errors (backpropagation) is used to train the network's weights and thresholds. This algorithm requires a disproportionately long training time during initial model creation.

5. The Support Vector Machine (SVM) algorithm attempts to optimize classification by maximizing the distance between the margins of classes. There are both linear and non-linear versions of this classifier, the latter of which is specifically designed for classes that cannot be linearly separated.

All machine learning algorithms were implemented using Python's Scikit-Learn library with the exception of the multilayer perceptron, which was implemented in Weka.

Algorithm and Model Evaluation

A learning curve is a plot of training and cross-validation accuracy as a function of the number of training data used. That is, a learning curve measures how much better a classification model is at predicting as the number of instances used to train that model is increased. Learning curves can also be used to gauge how well a model might perform when faced with new, previously unseen data by comparing training and testing accuracies and noting the degree of convergence. A model is said to have suffer from high bias if its accuracy is low, and is said to have suffer from high variance if its training and testing accuracies are dissimilar. A high-variance model is very sensitive to the sample used to build that model; its error depends in large part on the training set used, and as that error is evaluated across distinct cross-validation folds, the resulting variance in error is high. Models in this example were assessed using both classification accuracy and the degree to which testing accuracy converged with training accuracy.

According to an embodiment, the accuracy of the NOC model classifications (e.g. 1, 2, 3 or 4 contributors) was determined through comparison of the results obtained from the classification of the testing data set with the known number of contributors. Correct calls represent that class (number of contributors) that yields the highest probability compared to the known number of contributors. For example, given the results for a hypothetical sample A: Pr(class)=probability of A being a member of the class.

Given Pr(NOC:1)=0.000117; Pr(NOC:2)=0.000154; Pr(NOC:3)=0.977103; Pr(NOC:4)=0.022627, the PACE model classifies sample A as a mixture with three contributors; if the known number of contributors is three, the sample is identified as a correct classification.

It should be noted that in any system's attempt to classify the number of contributors in a DNA mixture, such a system will necessarily overestimate its own accuracy for the highest-numbered class in its associated data set. The lowest-numbered class for DNA mixture interpretation is one, but any chosen upper bound for a system's ability to classify the number of contributors is less than the number of contributors in some hypothetical mixture. The method described herein can be configured to evaluate primarily mixtures of 1-4 contributors, but 5- and 6-contributor mixtures are plausible samples, as are even more complicated mixtures. A modified system that evaluated mixtures of 1-6 contributors would still be unable to differentiate a 7-contributor sample, and so on. These mixtures with larger numbers of contributors would serve as a source of incorrect classification if they were present, especially when they contain confounding characteristics such as allele sharing. Their absence at the upper end of a system's classification limit therefore leads to overestimation of the system's accuracy at that upper limit.

According to an embodiment, the training data set evaluated in this example contained mixtures of 1, 2, 3, and 4 contributors; if a significant number of 5- and 6-contributor samples were included, some of the samples currently (correctly) classified as four NOC would likely be misclassified when the model is forced to consider a larger number of possible classes. Similarly, 5- and 6-contributor samples might be incorrectly classified as 4-contributor samples. One way to indirectly account for overestimation of 4-contributor classification accuracy is to observe that same overestimation in 3-contributor classification when all 4-contributor samples are removed. The reduction in accuracy for 3-person mixture classification can be considered a plausible lower bound for reduction in this study's 4-contributor classification accuracy.

Results

Kullback-Leibler divergence was calculated for ten candidate features, see TABLE 2, and the base pair size of a locus was removed from the list of candidate features after achieving a divergence of 0. All other features were kept, and used in subsequent machine learning. Summary metrics for all learning algorithms are found in TABLE 3.

TABLE 2

Kullback-Leibler divergence of nine candidate features.

| DKL | features |
| --- | --- |
| 1.638 | sample-wide peak count |
| 1.308 | maximum number of contributors |
| 1.060 | minimum number of contributors |
| 0.823 | template DNA amplified |
| 0.512 | locus-specific peak count |
| 0.358 | min/max observed peak heights |
| 0.309 | probability of dropout |
| 0.090 | minimum observed peak height |
| 0.038 | maximum observed peak height |
| 0 | size of locus |

TABLE 3

Summary metrics for six machine learning algorithms ("Classifier").

| Classifier | Number of Contributors | Precision | Recall | f1-score | Informedness | Training/testing Accuracy |
|---|---|---|---|---|---|---|
| k-NN | 1 | 0.96 | 0.99 | 0.98 | 0.940 | 0.981/0.955 |
|  | 2 | 0.98 | 0.97 | 0.97 |  |  |
|  | 3 | 0.98 | 0.87 | 0.92 |  |  |
|  | 4 | 0.79 | 0.98 | 0.88 |  |  |
| CART | 1 | 0.97 | 1.00 | 0.98 | 0.965 | 0.974/0.975 |
|  | 2 | 0.98 | 0.98 | 0.98 |  |  |
|  | 3 | 0.99 | 0.93 | 0.96 |  |  |
|  | 4 | 0.93 | 0.98 | 0.96 |  |  |
| Logistic regression | 1 | 0.97 | 0.98 | 0.97 | 0.949 | 0.963/0.961 |
|  | 2 | 0.97 | 0.98 | 0.98 |  |  |
|  | 3 | 1.00. | 0.89 | 0.94 |  |  |
|  | 4 | 0.83 | 1.00 | 0.90 |  |  |
| MLP | 1 | 0.97 | 0.96 | 0.96 | 0.943 | 0.970/0.962 |
|  | 2 | 0.96 | 0.97 | 0.96 |  |  |
|  | 3 | 0.96 | 0.95 | 0.96 |  |  |
|  | 4 | 0.95 | 1.00 | 0.97 |  |  |
| SVM (linear) | 1 | 0.91 | 0.96 | 0.94 | 0.842 | 0.912/0.894 |
|  | 2 | 0.89 | 0.90 | 0.89 |  |  |
|  | 3 | 0.89 | 0.77 | 0.82 |  |  |
|  | 4 | 0.88 | 0.96 | 0.92 |  |  |
| SVM (non-linear) | 1 | 0.96 | 0.99 | 0.97 | 0.957 | 0.982/0.971 |
|  | 2 | 0.98 | 0.97 | 0.97 |  |  |
|  | 3 | 1.00 | 0.93 | 0.96 |  |  |
|  | 4 | 0.93 | 1.00 | 0.96 |  |  |

Sample sizes for each class in the testing data set are as follows: 94 samples with 1 contributor, 155 samples with 2 contributors, 74 samples with 3 contributors, and 29 samples with 4 contributors. The total testing set (352 samples) included 753 sample-locus instances in 159 samples where allele dropout occurred (using the PACE dynamic analytical threshold). A non-linear support vector machine using a radial basis function kernel produces a tightly converging model with high classification accuracy rates; it scores second-highest of all classifiers in both convergence and accuracy, and lacks the tendency to over fit associated with CART, making it the preferred candidate for subsequent analysis.

Figure 3:
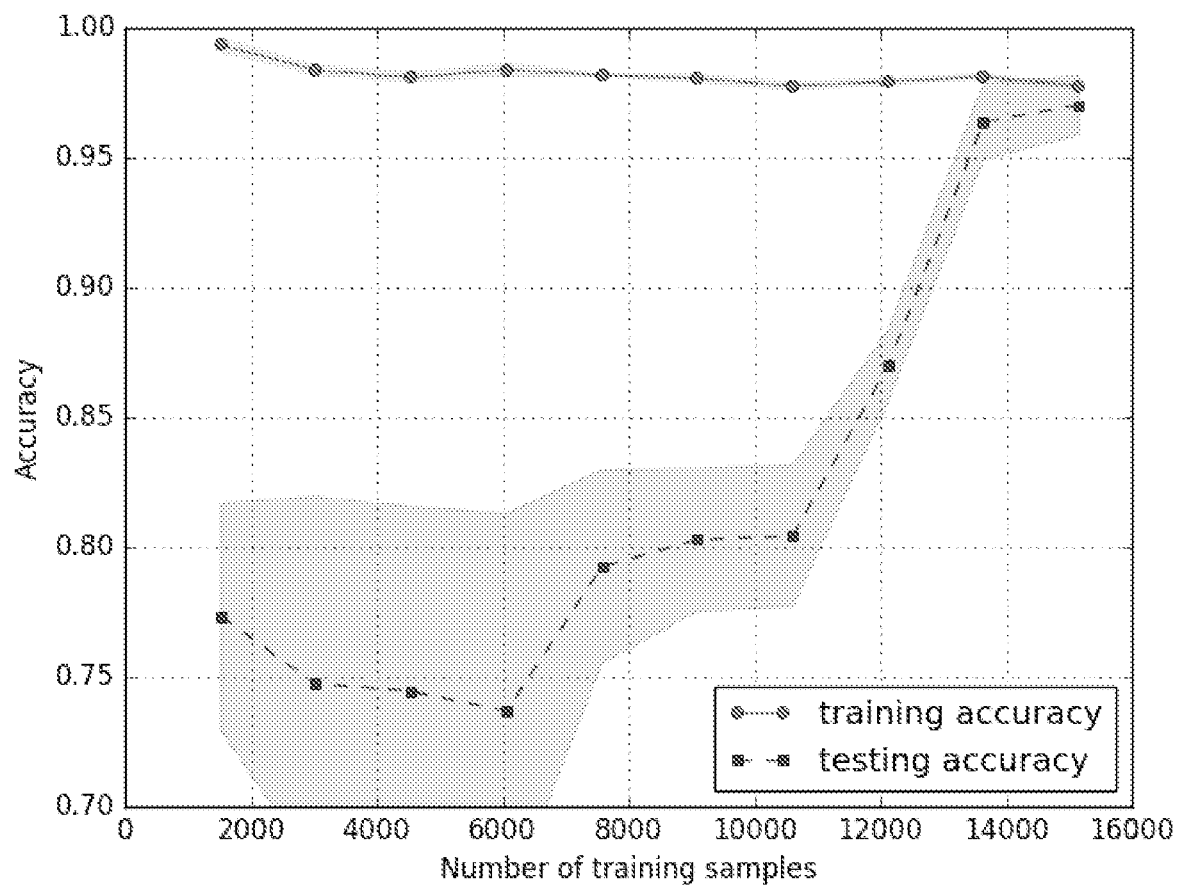
FIG. 3 is a graph of the learning curve for a method for DNA mixture analysis, in accordance with an embodiment.

Referring to FIG. 3, in one embodiment, is a graph of the learning curve for the kernel-based SVM model, illustrating model convergence for the top-performing algorithm's model.

Figure 4:
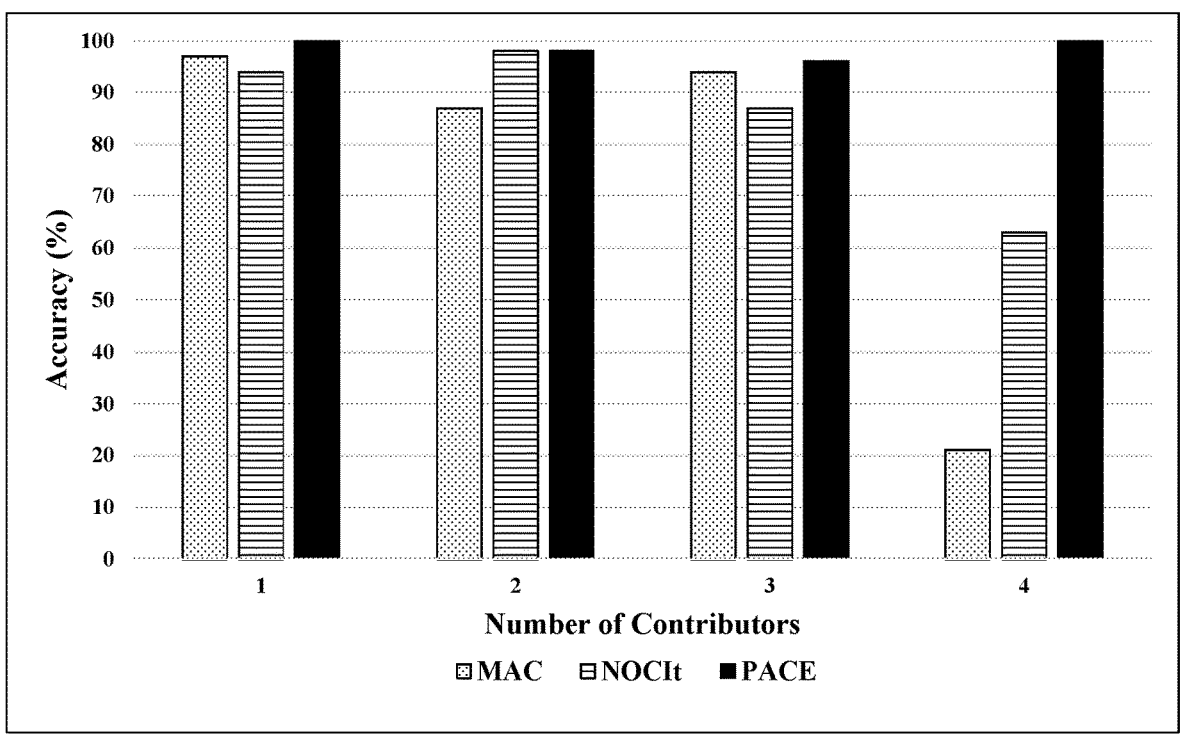
FIG. 4 is a graph of the performance of an embodiment of the method for DNA mixture analysis compared to the prior art methods, in accordance with an embodiment.

Referring to FIG. 4, in one embodiment, is a graph of the performance of the Support Vector Machine (SVM) algorithm compared to the maximum allele count (MAC) method, as well as to results from NOCK The SVM-derived model outperformed MAC in all cases, performed similarly to NOCit for one- and two-contributor samples, and strongly outperformed NOCit for three- and four-contributor samples, including running ~3,600 times faster (~9 hours vs. ~9 seconds). The maximum allele count (MAC) method requires the identification of the locus or loci with the maximum number of allelic peaks, and the minimum number of contributors is then calculated by counting the number of allelic peaks divided by 2 (to account for ploidy) and rounding up to the nearest whole number. The MAC method does not work well with complex mixtures in large part due to the potential for allele sharing between contributors. The NOCit method infers the number of contributors in a DNA sample through calculating the posterior probability via a Monte Carlo-based approach. This method utilizes both qualitative and quantitative data regarding the DNA sample for its inferences. However, NOCIt requires extensive processing time; a five-person mixture may take up to 9 hours to evaluate, which can be prohibitive in a forensic lab requiring rapid analysis of backlogged casework. Further, the correct estimation rate for the number of contributors in a DNA mixture using either MAC or NOCIt arguably remains unacceptably poor as the number of contributors to be identified increases.

Training and testing sets were compiled from the aforementioned samples using a proportionally stratified sampling of the overall data set. See TABLES 4 and 5. Stratified sampling was used to ensure a proportional representation of each contributor class in the two distinct sample sets.

TABLE 4

Sampling Structure for the training and testing data sets based on the amount of DNA template amplified (ng).

| | Training Set | | | Testing Set | | |
|---|---|---|---|---|---|---|
| DNA Template Amplified (ng) | Sample-Locus Instance Count | Sample Count | Percent Representation | Sample-Locus Instance Count | Sample Count | Percent Representation |
| 0.0125 | 100 | 6 | 0.4% | 0 | 0 | 0.0% |
| 0.025 | 153 | 10 | 0.7% | 31 | 2 | 0.6% |
| 0.05 | 235 | 15 | 1.1% | 31 | 2 | 0.6% |
| 0.0625 | 1152 | 72 | 5.1% | 253 | 16 | 4.6% |
| 0.075 | 287 | 18 | 1.3% | 64 | 4 | 1.1% |
| 0.1 | 303 | 19 | 1.4% | 159 | 10 | 2.8% |
| 0.125 | 1211 | 76 | 5.4% | 319 | 20 | 5.7% |
| 0.15 | 2800 | 175 | 12.5% | 694 | 43 | 12.3% |
| 0.2 | 768 | 48 | 3.4% | 128 | 8 | 2.3% |
| 0.25 | 1360 | 85 | 6.1% | 416 | 26 | 7.4% |
| 0.3 | 224 | 14 | 1.0% | 112 | 7 | 2.0% |
| 0.4 | 528 | 33 | 2.4% | 160 | 10 | 2.8% |
| 0.5 | 3216 | 201 | 14.3% | 848 | 53 | 15.1% |
| 0.6 | 96 | 6 | 0.4% | 32 | 2 | 0.6% |
| 0.7 | 272 | 17 | 1.2% | 48 | 3 | 0.9% |
| 0.8 | 336 | 21 | 1.5% | 48 | 3 | 0.9% |
| 1 | 3938 | 246 | 17.5% | 944 | 59 | 16.8% |
| 1.2 | 96 | 6 | 0.4% | 48 | 3 | 0.9% |

TABLE 4-continued

Sampling Structure for the training and testing data sets based on the amount of DNA template amplified (ng).

| DNA Template Amplified (ng) | Training Set | | | Testing Set | | |
|---|---|---|---|---|---|---|
| | Sample-Locus Instance Count | Sample Count | Percent Representation | Sample-Locus Instance Count | Sample Count | Percent Representation |
| 1.3 | 80 | 5 | 0.4% | 16 | 1 | 0.3% |
| 1.5 | 320 | 20 | 1.4% | 48 | 3 | 0.9% |
| 1.6 | 48 | 3 | 0.2% | 16 | 1 | 0.3% |
| 1.7 | 128 | 8 | 0.6% | 32 | 2 | 0.6% |
| 2 | 1552 | 97 | 6.9% | 336 | 21 | 6.0% |
| 2.5 | 192 | 12 | 0.9% | 64 | 4 | 1.1% |
| 3 | 384 | 24 | 1.7% | 144 | 9 | 2.6% |
| 3.3 | 96 | 6 | 0.4% | 16 | 1 | 0.3% |
| 3.5 | 96 | 6 | 0.4% | 32 | 2 | 0.6% |
| 4 | 1443 | 90 | 6.4% | 304 | 19 | 5.4% |
| 5 | 192 | 12 | 0.9% | 48 | 3 | 0.9% |
| 6 | 256 | 16 | 1.1% | 64 | 4 | 1.1% |
| 7 | 320 | 20 | 1.4% | 112 | 7 | 2.0% |
| 7.5 | 48 | 3 | 0.2% | 16 | 1 | 0.3% |
| 8 | 96 | 6 | 0.4% | 0 | 0 | 0.0% |
| 9 | 96 | 6 | 0.4% | 32 | 2 | 0.6% |
| 10 | 32 | 2 | 0.1% | 0 | 0 | 0.0% |
| Total | 22454 | 1404 | | 5615 | 351 | |

TABLE 5

Sample sets used for the training and testing of NOC classification models created by machine learning algorithms.

| Contributor Number | Training Set | | Testing Set | |
|---|---|---|---|---|
| | Sample Count | Percentage | Sample Count | Percentage |
| 1 | 378 | 26.9% | 94 | 26.8% |
| 2 | 607 | 43.3% | 154 | 43.9% |
| 3 | 276 | 19.7% | 74 | 21.1% |
| 4 | 142 | 10.1% | 29 | 8.3% |
| Total | 1403 | | 351 | |

The contributor classes (e.g. 1, 2, 3 or 4 contributors) were proportionally represented in the training and testing sets, with no overlap in the samples included in each set; classifications resulting from the samples in the testing set are therefore independent of the samples used to create the model. The overall model accuracy is 98.5%, meaning that 98.5% of the sample classifications (i.e. 1, 2, 3 or 4 contributors) were correct based on a comparison of the model's classifications with the known number of contributors. Classification of unknown single source and 4-contributor samples yielded 100% accuracy, with 94 and 29 samples, respectively. The 2- and 3-contributor samples displayed 98.1% (152/155) and 95.9% (71/74) accuracy, respectively. See, TABLES 6A and 6B.

TABLE 6A

Number of contributor classification model accuracy rates when used to classify samples from the testing set.

| Contributor # | % Correct | Incorrect Count | Correct Count | Over-estimate | Under-estimate |
|---|---|---|---|---|---|
| 1 | 100% | 0 | 94 | 0 | 0 |
| 2 | 98.1% | 3 | 152 | 0 | 3 |
| 3 | 95.9% | 3 | 71 | 1 | 2 |
| 4 | 100% | 0 | 29 | 0 | 0 |

TABLE 6B

A confusion matrix representing the classifications of those data by PACE.

| | | Predicted Number of Contributors | | | |
|---|---|---|---|---|---|
| | | 1 | 2 | 3 | 4 |
| Actual Number of Contributors | 1 | 94 | 0 | 0 | 0 |
| | 2 | 3 | 152 | 0 | 0 |
| | 3 | 0 | 2 | 71 | 1 |
| | 4 | 0 | 0 | 0 | 29 |

All samples with incorrect classifications were misclassified by a maximum of ±1 contributor; for example, the 3 misclassifications in the 2-contributor group were misclassified as a single source, and the 3 samples misclassified in the 3-contributor group were classified as either 2-contributor or 4-contributor samples. FIGS. 3 and 4 display the accuracy of the model across the DNA template (ng) amplified, with expanded data regarding misclassification shown in Table 5, with the ratio of contributors further explaining the misclassifications given the DNA template amount per contributor within a sample. (As anticipated, 3 of the 6 misclassifications occur at low DNA template amounts, at or below 0.25 ng of template DNA amplified, which is below the typical 1.0 ng target template amount for single source samples. The 2-contributor misclassified samples with 2.0 ng of template DNA amplified were both mixtures of 2 contributors at a 1 to 19 ratio, therefore the minor component is expected to contribute approximately 0.1 ng total to the mixture. Additionally, these two samples exhibit nearly equal probabilities in the 1 and 2 contributor classes shown in TABLE 7.

TABLE 7

Summary of misclassifications by the NOC classification model.

| Contributor Number | Sample ID | DNA Template (ng) | Ratio of Contributors | Percentage of Dropout | PACE Model Estimate | PACE Contributor Probabilities | | | |
|---|---|---|---|---|---|---|---|---|---|
| | | | | | | Pr(1) | Pr(2) | Pr(3) | Pr(4) |
| 2 | 225 | 2.0 | 1 to 19 | 9.3 | 1 | 0.53808 | 0.46164 | 0.00028 | 0.00000 |
| | 226 | 2.0 | 1 to 19 | 14.0 | 1 | 0.55271 | 0.44729 | 0.00000 | 0.00000 |
| | 295 | 0.0625 | 1 to 19 | 34.9 | 1 | 0.92698 | 0.07302 | 0.00000 | 0.00000 |

TABLE 7-continued

Summary of misclassifications by the NOC classification model.

| Contributor Number | Sample ID | DNA Template (ng) | Ratio of Contributors | Percentage of Dropout | PACE Model Estimate | PACE Contributor Probabilities | | | |
|---|---|---|---|---|---|---|---|---|---|
| | | | | | | Pr(1) | Pr(2) | Pr(3) | Pr(4) |
| 3 | 317 | 7.0 | 3 to 1 to 1 | 0 | 4 | 0.00791 | 0.01679 | 0.01650 | 0.95880 |
| | 251 | 0.15 | 1 to 1 to 3 | 21.7 | 2 | 0.00865 | 0.88060 | 0.00208 | 0.00000 |
| | 262 | 0.25 | 1.5 to 3 to 1 | 22.4 | 2 | 0.00211 | 0.99549 | 0.00240 | 0.00000 |

Figure 5:
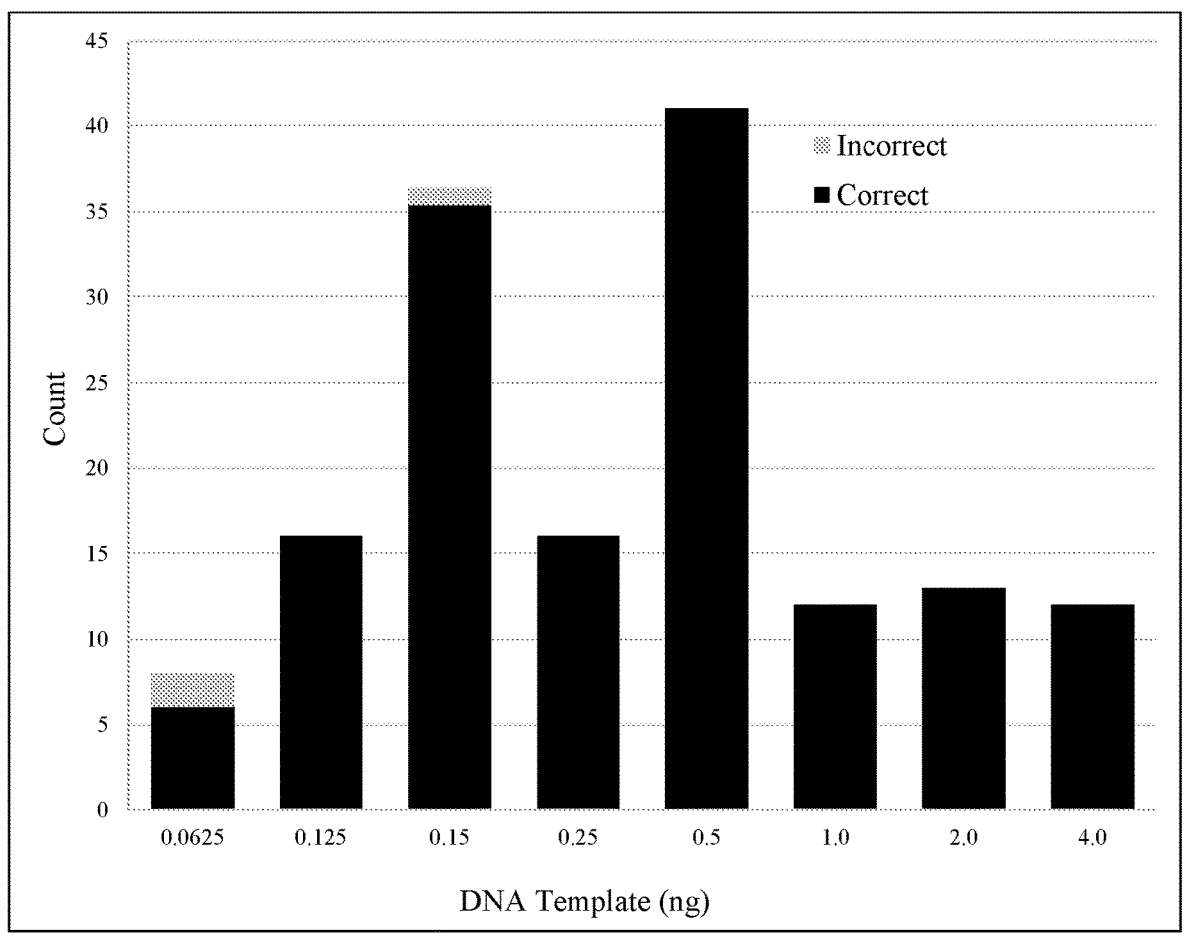
FIG. 5 is a graph of the accuracy of an embodiment of the method for DNA mixture analysis, in accordance with an embodiment.
Figure 6:
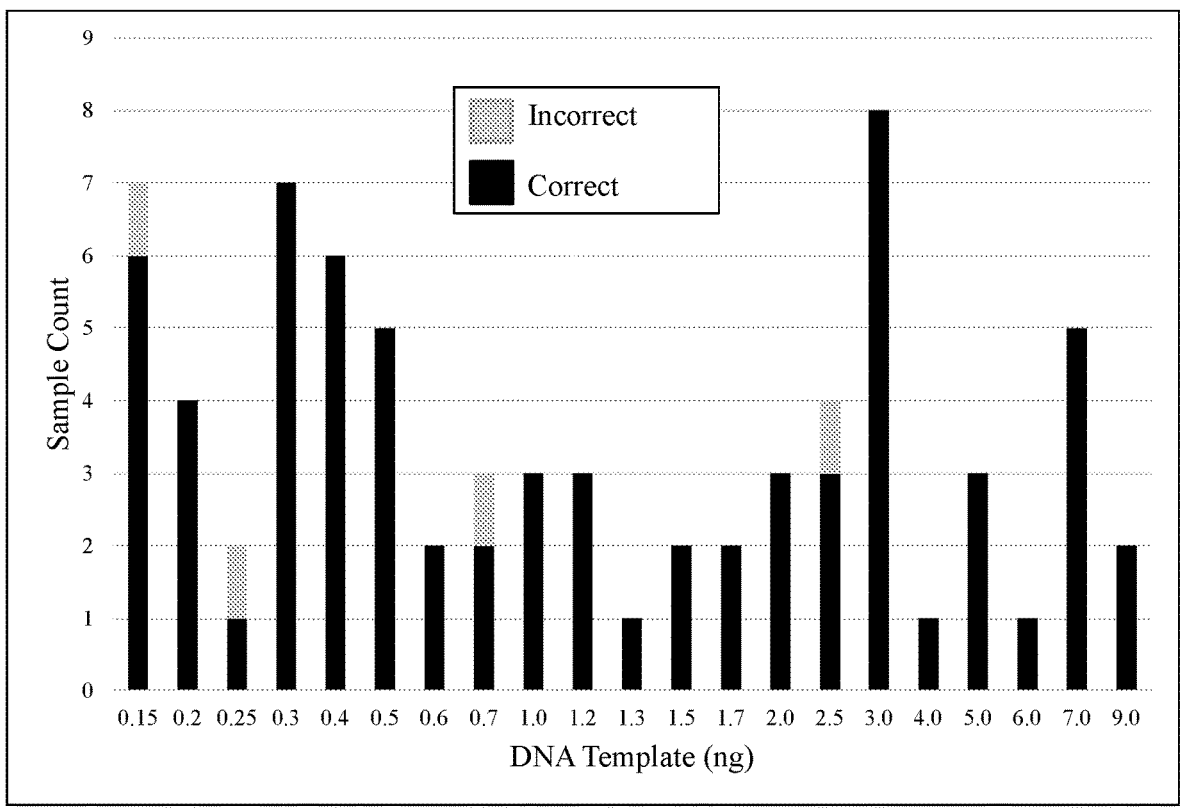
FIG. 6 is a graph of the accuracy of an embodiment of the method for DNA mixture analysis, in accordance with an embodiment.

Referring to FIG. 5, in one embodiment, is a graph of the accuracy of the characterization method described or otherwise envisioned herein, using amplified DNA template (ng). Similarly, referring to FIG. 6, in one embodiment, is a graph of the accuracy of the characterization method described or otherwise envisioned herein, using amplified DNA template (ng). As anticipated, 6 of the 7 misclassifications using the method occur below 0.75 ng of template DNA amplified.

A second model created from a machine learning algorithm exposed only to 1-3 contributor DNA samples was compared to the primary model described above, which was learned from an algorithm exposed to the entire data set (1-4 contributors), with resulting classification accuracy rates shown in Table 7. A "1-3 contributors" model should overestimate the accuracy of 3-person mixture classification, and a comparison of the two models' accuracy rates for 3-person mixtures provides a potential lower bound of overestimation for the highest-numbered class in a model. A reduction in classification accuracy for 3-person mixtures of 2% was observed, suggesting that the primary model's 4-person classification accuracy is likely overestimated by at least the same amount.

Discussion

The proposed probabilistic method for estimating the number of contributors is a robust and reproducible method that was developed using an expansive data set comprised of samples amplified using the AmpFLSTR® Identifiler® PCR Amplification Kit (ThermoFisher Scientific Inc.). Our focus on the Identifiler® data set was due to current availability of samples; however, the method is applicable to any amplification system in use. Similar training data sets can be compiled from multiple laboratories' validation studies, with additional samples run as needed. A noteworthy aspect of this method is its independence based on instrument and injection parameters. The data presented were compiled from 5 different capillary electrophoresis instruments at 2 different laboratories, and had varied injection times (2 to 22 seconds) and kV used for injection (1 to 5 seconds). This is a significant advantage that would permit the model to be easily transferred between laboratories and would not require significant resources to perform internal validation.

According to an embodiment, the data set utilized to train the algorithm could include, for example, degraded and inhibited samples. The utilized data set contained low template samples (0.0125 ng-0.0625 ng) that experienced a level of degradation common for such samples. Although it is believed that these data should be added to the training set, due to the presence of these low template samples that display typical degradation patterns, it is anticipated that the effect will have minimal impact on the generalizability or overall accuracy to classify unknowns.

While eight of the nine initial candidate features were retained for machine learning, it should be noted that these are merely an initial set of candidates that impacted successful classification. Other candidates could increase (or decrease) classification accuracy if included. Of specific interest would be the inclusion of features more commonly associated with the process of mixture deconvolution; it may be that the mixture ratios of high-probability genotype combinations for a given sample, for example, contains information not found in the feature vector described here that nonetheless impacts NOC classification. Accordingly, the methods described or otherwise envisioned herein are specifically designed to be feature agnostic, and can construct classification models using feature vectors containing any type of data, be they numeric, nominal, binary, or even character-based.

Most of the candidate machine learning algorithms evaluated in this study produced similar accuracy rates and variances. A linear support vector machine performed noticeably worse, suggesting that the data are poorly separable using a linear decision boundary. While a non-linear SVM exhibited the highest classification accuracy, a secondary benefit of using such a learning algorithm for model construction is its tendency to generalize well; in comparison, decision trees and k-NN classifiers are known for greater likelihood of learning models that overfit training data.

The overall accuracy of the model across all testing samples is over 98.5%, with only 6 misclassifications observed in the 2- and 3-contributor sample groups. The 100% accuracy experienced in the 4-contributor group is in part due to the lack of 5 (or greater) contributor samples for training; this group can be more accurately considered a "≥4 contributor" group. Based on analysis of overestimation for 1 to 3 contributor classification, this model's accuracy would be expected to drop by at least 2% from the observed 100% classification accuracy if 5 contributor samples are included in the training data, for example. The practical utility of classifying a profile with having ≥4 contributors is significant, as many laboratories choose to not interpret DNA profiles with greater than 3 contributors.

The method described or otherwise envisioned herein is proposed as a valuable tool in the analyst assessment of the number of contributors. Of the 6 misclassifications (out of 352 total samples), 3 of the samples could be corrected if an analyst briefly reviewed the data, through the identification of artifactual peaks such as minus A and pull-up and indications of peaks below thresholds. The remaining 3 instances were due to allele dropout, allele sharing and high template effects such as elevated stutter, whereas an analyst or software did not have significant evidence to accurately predict the number of contributors. With analyst input the model has an accuracy rate of over 99.0% when evaluated using the testing data set. In addition, if imposing a threshold of a probability of 99.0% only 1 sample would be incorrectly classified in both the full testing set and the truncated—degradation testing set.

According to one embodiment, the system can comprise a single unit with one or more modules, or may comprise multiple modules in more than one location that may be connected via a wired and/or wireless network connection. Alternatively, information may be moved by hand from one module to another. The system may be implemented by hardware and/or software, including but not limited to a processor, computer system, database, computer program, and others. The hardware and/or software can be implemented in different systems or can be implemented in a single system.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

A "module" or "component" as may be used herein, can include, among other things, the identification of specific functionality represented by specific computer software code of a software program. A software program may contain code representing one or more modules, and the code representing a particular module can be represented by consecutive or non-consecutive lines of code.

As will be appreciated by one skilled in the art, aspects of the present invention may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowcharts/block diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some 23 alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A system configured to characterize a number of contributors to a DNA mixture within a sample, the system comprising:
    a sample preparation module configured to generate initial data about the DNA mixture within the sample;
    a processor comprising a number of contributors determination module, wherein the number of contributors determination module comprises a machine-learning algorithm configured to: (i) receive the generated initial data; (ii) analyze the generated initial data to determine the number of contributors to the DNA mixture within the sample, wherein the machine learning algorithm is trained to evaluate the initial data to determine the number of contributors based on a set of candidate features including all of a sample-wide peak count, a maximum number of contributors, a minimum number of contributors, a locus-specific peak count, a probability of dropout, a minimum observed peak height, and a maximum observed peak height; and
    an output device configured to receive the determined number of contributors from the processor.

2. The system of claim 1, wherein the machine-learning algorithm comprises a support vector machine algorithm.

3. The system of claim 1, wherein the output device comprises a monitor.

4. The system of claim 1, wherein the sample preparation module comprises amplification of DNA within the sample.

5. The system of claim 1, wherein the sample preparation module comprises amplification of one or more DNA markers within the sample.

6. A system configured to characterize a number of contributors to a DNA mixture within a sample, the system comprising a processor configured to receive data about the DNA within the sample, and further configured to analyze, using a machine-learning algorithm, the received data to determine the number of contributors to the DNA mixture within the sample, wherein the machine learning algorithm is trained to evaluate the data to determine the number of contributors based on a set of candidate features including all of a sample-wide peak count, a maximum number of contributors, a minimum number of contributors, a locus-specific peak count, a probability of dropout, a minimum observed peak height, and a maximum observed peak height.

7. The system of claim 6, further comprising a sample preparation module configured to generate the data about the DNA within the sample.

8. The system of claim 7, wherein the sample preparation module comprises amplification of DNA within the sample.

9. The system of claim 7, wherein the sample preparation module comprises amplification of one or more DNA markers within the sample.

10. The system of claim 6, further comprising an output device in communication with the processor, the output device configured output information about the received determined number of contributors.

11. The system of claim 10, wherein the output device comprises a monitor.

12. The system of claim 6, wherein the machine-learning algorithm comprises a support vector machine algorithm.

* * * * *